Figure 1:
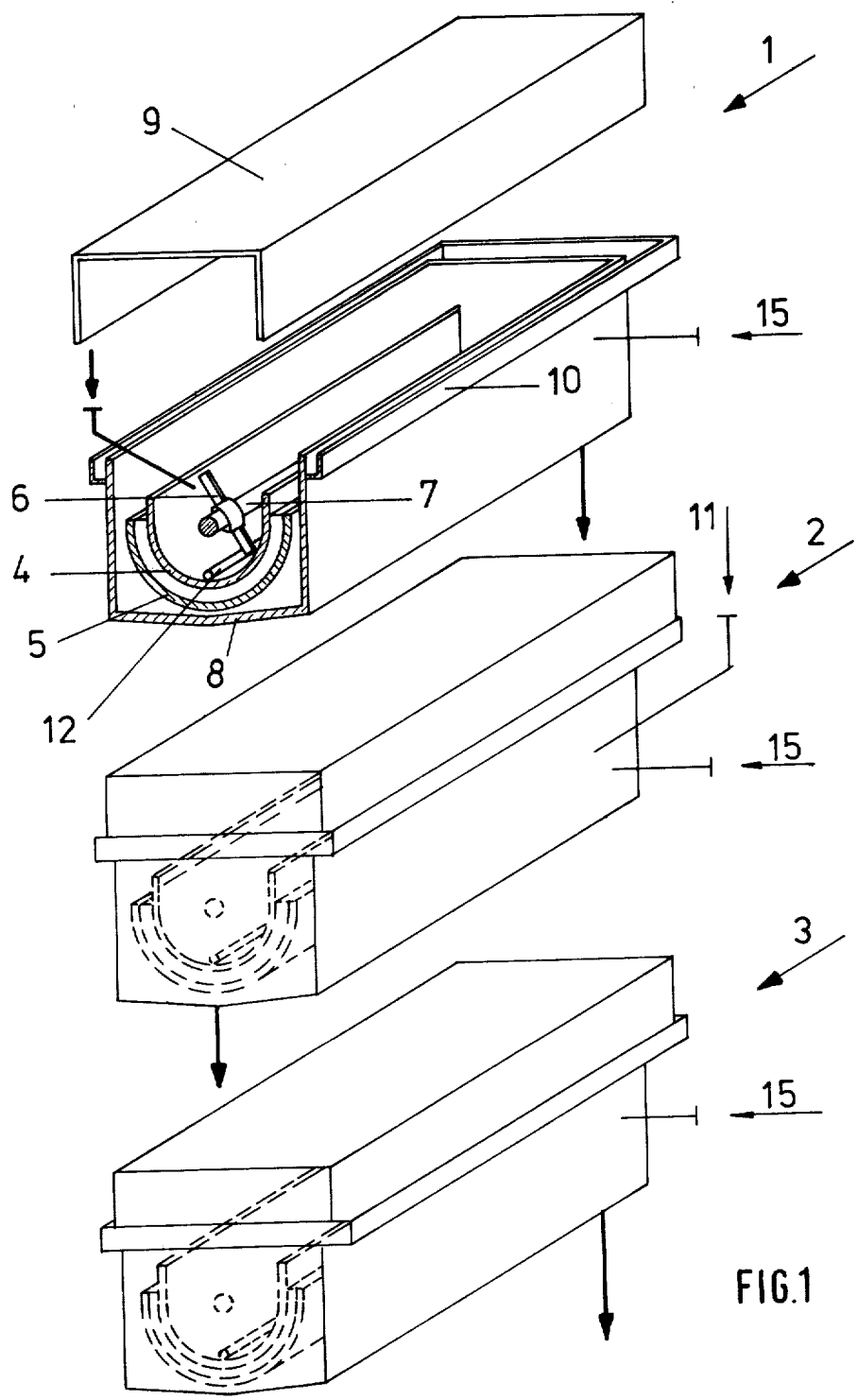

United States Patent [19]

Thoma

[11] 4,390,726

[45] Jun. 28, 1983

[54] PROCESS FOR THE PRODUCTION OF GUANIDINE NITRATE FROM A MIXTURE OF UREA AND AMMONIUM NITRATE AND APPARATUS FOR ITS PERFORMANCE

[75] Inventor: Matthias Thoma, Waldkraiburg, Fed. Rep. of Germany

[73] Assignee: Industrie Chemie Thoma GmbH & Co. Produktions KG, Waldkraiburg, Fed. Rep. of Germany

[21] Appl. No.: 247,512

[22] Filed: Mar. 25, 1981

[30] Foreign Application Priority Data

Mar. 25, 1980 [DE] Fed. Rep. of Germany ....... 3011333

[51] Int. Cl.$^3$ .......................................... C07C 128/00
[52] U.S. Cl. .................... 564/242; 544/194; 252/449
[58] Field of Search ......................................... 564/242

[56] References Cited

U.S. PATENT DOCUMENTS 2,258,612  10/1941  Jayne et al. ......................... 564/242
2,468,067   4/1949  Hill ..................................... 564/242
2,949,484   8/1960  Mackay .
3,043,878   7/1962  Roberts et al. ..................... 564/242

FOREIGN PATENT DOCUMENTS 1141635  12/1962  Fed. Rep. of Germany .

*Primary Examiner*—Natalie Trousof
*Assistant Examiner*—L. Hendriksen

*Attorney, Agent, or Firm*—Fleit, Jacobson & Cohn

[57] ABSTRACT

In a process for the production of guanidine nitrate from a mixture of urea and ammonium nitrate in the presence of a catalyst containing silicium oxide at increased temperature, the initial mixture of urea and ammonium nitrate having an excess of ammonium nitrate, urea is added stepwise to the existing mixture of urea and ammonium nitrate and the catalyst during the procedure in quantities so that the weight ratio of urea: ammonium nitrate is permanently in favor of an excess of ammonium nitrate. The weight ratio is practically maintained during the process and is increased only in the final phase. An apparatus for the performance of the process of the invention comprises a reactor system including one or several substantially horizontal, tubular, heatable reactors in a series. The reaction mass is introduced together with the catalyst in the form of a melt and moved through the reactor system by means of a stirrer and a conveyor. At one or several places before the outlet of the reactor system inlet nozzles are provided in certain distances from one to the other through which urea and catalyst may be added to the melt.

For a continuous performance for the process the reaction mass is brought onto heatable conveyor belts in a series as a layer of the desired thickness. Along the belt the required additives are added to the reaction mass. The rate of the conveyor belts depends on the reaction rate.

17 Claims, 2 Drawing Figures

PROCESS FOR THE PRODUCTION OF GUANIDINE NITRATE FROM A MIXTURE OF UREA AND AMMONIUM NITRATE AND APPARATUS FOR ITS PERFORMANCE

This invention provides a process for the production of guanidine nitrate from a mixture of urea and ammonium nitrate in the presence of a catalyst containing silicium oxide at an increased temperature, the initial mixture of urea and ammonium nitrate having an excess of ammonium nitrate and the formed guanidine nitrate being separated off. Furthermore the invention provides apparatus for its performance.

It is already known to pass a molten mixture of urea and ammonium nitrate in a molecular ratio of 1:1 to 1:6, preferable 1:2 to 1:3, under normal pressure and a temperature of approx. 175°–225° C. and preferable 190°–200° C. through a vertical column containing the catalyst and to isolate the formed guanidine nitrate in a well-known manner to produce guanidine nitrate. In this process the unreacted nitrate and urea compositions are separated from the formed guanidine nitrate compound and mixed with fresh initial material and again passed through the catalyst. A preferred catalyst in the well-known process is a gel of silicic acid.

The reaction may be theoretically represented by the below equation:

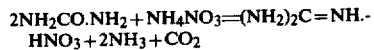

$$2NH_2CO.NH_2 + NH_4NO_3 = (NH_2)_2C=NH.HNO_3 + 2NH_3 + CO_2$$

In the well-known procedure the initial melt from urea, ammonium nitrate and mother liquor residue is passed through a tubular reactor with a diameter of 2.5 cms which contains the catalyst containing the silicic acid as a gel bed of 15–61 cms height, preferably 61 cms on the grounds of the higher yields of guanidine nitrate which may be achieved hereby. The obtained guanidine nitrate is dissolved in hot water, subsequently cooled to room temperature and separated off by means of a centrifuge and dried. The optimum yield is indicated with 89% related to the employed urea.

The well-known process, however, is not suitable for use in industry because the described ratios cannot be transferred to the industrial production of guanidine nitrate. Moreover considerable disadvantages adhere to the well-known process which make the process dangerous due to the risk of explosion. The circulating melt is enriched continuously with organic and inorganic impurities caused by the reflux of the mother liquor residue and particularly by the increasing occupation of the catalyst. This may result in a spontaneous disintegration of the urea/ammonium nitrate mixture. The catalyst present in the reactor column initially available in a coarse form is increasingly exhausted and is dissolved into a slurry which is carried out together with the reaction mixture. Hereby the dusty catalyst also enters the precipitated guanidine. Its separation is no longer possible by a simple method. From the continuous disintegration of the catalyst there further result decreasing conversion rates and thus a reduced yield unless the catalyst can be made up continuously. This, however, is undesirable for economic reasons because the catalyst is about ½ times more expensive than the final product.

In example 1 described in the German patent application DAS 1 141 635 it is indicated that in a working period of 11 days 3.229 kgs of guanidine nitrate are produced if the described reaction vessel is equipped with a tube of 2.5 cms diameter and a bed of a silicic acid gel 61 cms high is used. However, this means that only a guanidine nitrate yield of 49 grs per hour can be achieved whereby only 33% of the used urea and 10% of the employed ammonium nitrate were actually converted. This is shown when calculating on the basis of example 1.

In order to use the well-known process industrially, the inner diameter of the reactor tube would have to be increased but because of the required supply and discharge of heat there are limitations for enlarging this tube. To obtain a high production rate as desired, there would be a chance to equip the reactor with a large number of parallel operated tubes but in this case each tube would require a dosing device of its own to guarantee an even throughput through each reactor tube. Nevertheless it may well be that with gradual exhaust of the catalyst it clogs any of the tubes for the passage of the melt at an early stage and thus the passage of the melt through the other pipes is speeded up and the desired conversion and the optimum yield are not obtained. Furthermore the catalyst is continuously enriched with triazines in this case and thus also continuously its activity is decreased.

Furthermore it is to be pointed out that with the required conversion temperatures of approx. 192° C., beside of the oxidation of 8–9% urea, increasingly triazines, particularly ammeline and ammelide are formed. The latter are nearly insoluble and cover the catalyst surface and thus its activity and the reactivity of the mixture is considerably decreased thus reducing the yield that could be obtained.

The purpose of the described invention is to provide a process for the production of guanidine nitrate from urea and ammonium nitrate permitting an economic industrial use. Another purpose is to obtain higher yields of the desired product with a low catalyst consumption. Furthermore apparatus are to be provided permitting an industrial performance of the invented process.

According to the invention these aims are achieved by the stepwise addition of urea to the present mixture of urea and ammonium nitrate in quantities so that the weight proportion of urea:ammonium nitrate up to the conversion of all the urea is always in favour of an excess of ammonium nitrate the amount of which practically remains the same during the procedure up to the final phase and only subsequently is increased in favour of the ammonium nitrate.

It has been found that the weight ratio of the urea-/ammonium nitrate mixture is decisive for an optimum yield of guanidine nitrate. During the process, however, the existing weight ratio of the reactants changes so that the initially optimum ratio is affected, i.e. lower yields are obtained. By the present invention, however, during the entire procedure, i.e. from the beginning of the conversion up to the approximate consumption of the urea, urea and ammonium nitrate are always present in the same ratio which can be chosen optimally on the grounds of the adjusted reaction temperature. This results in the fact that during the entire reaction the reactants are required only in quantities as actually converted in the molecular ratio. In any case it has been found that by the invented process a higher conversion rate and higher yields can be obtained than known previously.

Due to a stepwise addition of the catalyst it can be achieved at the same time that the probability of the catalyst effect for the reactants reacted together remains the same also during the time when the quantitative ratios of active reactants and already present reaction products are continuously changed. In particular, this also prevents that with proceeding reaction a reduced yield due to exhausted catalyst must be feared. From the above mentioned facts concerning the efficiency of the catalyst it is further seen that the catalyst preferably should be added in increasing quantities during the process basing on an optimal chosen initial quantity.

It has been found that at reaction temperatures between 180° C. and 190° C. optimum yields are achieved by a urea/ammonium nitrate ratio of approximately 1:2. If therefore preferably during the procedure the stepwise addition of urea is chosen at around ⅔ of the urea consumed during the formation of guanidine nitrate, it is achieved that during the entire conversion the urea-/ammonium nitrate ratio up to the final phase remains unchanged at 1:2 and only then it is increased to 1:5 to 1:6. Preferably the total quantity of the catalyst used for one batch is chosen with about 10-20% related to the employed mixture urea:ammonium nitrate.

According to another preferred performance of the process of the invention a part of the ammonium carbamate formed during the reaction of urea and ammonium nitrate is disintegrated into ammonia and $CO_2$ and a part of the obtained ammonia is passed through the reaction mixture. Hereby the pH figure of the mixture is increased from 9.0 to 9.3 up to approx. 9.8 to 10.2. Thus the guanidine nitrate content is increased so that more than 94% yield related to the consumed urea is obtained if the reaction temperature and the ratio of ammonium nitrate and urea are optimally chosen and maintained according to the invention. Another advantage is a reaction time that is 15-20% shorter. Furthermore less triazines are formed because during the same reaction period a higher excess of ammonium nitrate is present.

The performance of the process for the production of guanidine nitrate from ammonium nitrate and urea may be represented by the above equation.

According to a preferred performance of the invention the ammonia formed during the conversion is converted into ammonium nitrate by means of nitric acid according to the equation

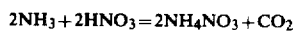

$$2NH_3 + 2HNO_3 = 2NH_4NO_3 + CO_2$$

After drying, the formed ammonium nitrate which is free of water is reused partly or entirely together with urea. Hereby, according to the invention, only pure or purified (as described below) ammonium nitrate is used. In this case it is of no importance whether working continuously or discontinuously. Thus it is avoided that during the operation impurities may increase which might represent a danger of a spontaneous disintegration of the melt under the existing reaction temperatures. Such danger of an explosion, however, exists in the already described process because in this process mother liquor residues containing the triazines formed in the conversion period are refluxed into the fresh melt whereas in the process of the invention they are purified first.

Furthermore by the use of always fresh or purified ammonium nitrate from preceding batches foaming of the reaction mixture is prevented. Foaming may result in a spontaneous disintegration when refluxing mother liquor with foreign matter.

In the continuous but also in the discontinuous performance of the process of the invention preferably the catalyst is regenerated after a certain conversion—if required after each throughput—so that it can be reused as a fresh catalyst in the next passage of the process. Thus not only better economic efficiency is obtained due to lower catalyst consumption but the process also has the advantage of ascertained constant working conditions and thus optimalization of yields. The above mentioned regeneration of the catalyst can be carried out relatively easy. The catalyst is dehydrated at 50°-80° C. at 10-30 Torr and subsequently heated at 160°-200° C. and also 10-30 Torr whereby the last traces of water and also a part of the volatile organic matter are largely disintegrated and removed as a gas. For the complete regeneration (i.e. when the catalyst shows a deposit of approx. 5-10% produced by-products) the catalyst is heated to 320°-350° C. instead of 150°-200° C. under the same vacuum for a period of 2 to 3 hours but the crystalline lattice of the catalyst is not changed.

A preferred performance of the process of the invention is to separate from the catalyst the hot guanidine solution formed during the process and diluted with additional wash-water from preceding batches and to mix it with binders to bind the organic substances present in the solution and to separate them off by filtration. Then the filtrate contains only pure guanidine nitrate beside of ammonium nitrate and urea. This guanidine nitrate is precipitated by cooling the solution without recrystallization.

It has been found that in the performance of the process of the invention the yield related to used urea amounts to 87-90% and to 97% related to ammonium nitrate.

The filtrate contains about
40-45% of ammonium nitrate
8-12% of urea
2-3% of guanidine nitrate
rest being water By the addition of binders the impurities are precipitated and filtered off. By evaporating the wash-water under reduced pressure a guanidine nitrate free of water is obtained together with urea and ammonium nitrate which may be reused, if desired, together with the addition of approx. 60% fresh ammonium nitrate and 90% urea partly or totally.

As approx. 90% urea and 60% ammonium nitrate as well as regenerated catalyst (i.e. a catalyst free of triazines) are continuously passed into the guanidine nitrate production cycle, there is no danger that increasingly by-products are formed which might cause an undesired reaction or spontaneous disintegration of the reaction mixture.

The obtained guanidine nitrate has a purity of minimum 98.5-99.2%.

Another advantage of the process of the invention is that the filtrate obtained after separation of the guanidine crystals which filtrate contains 40-60% ammonium nitrate, 1-3% urea, 1-2% guanidine nitrate, 0.1-0.3% ammelide and ammeline, the rest being water, may be supplied to the fertilizer industry after it has been concentrated unless it is not intended to reuse it for the production of guanidine.

The continuous production of guanidine nitrate from urea and ammonium nitrate is carried out in suitable stirred autoclaves in series.

The ammonium nitrate to be reused totally or partly is obtained by converting the ammonium carbamate formed during the reaction of urea and ammonium nitrate into ammonium nitrate and $CO_2$ by means of nitric acid. The anhydrous ammonium nitrate is used together with urea in the process totally or partly depending on the use of the excessive ammonium nitrate from preceding batches.

Details of the process of the invention may be seen from the below examples, examples 1 and 2 describing the procedure with discontinuous conversion and examples 3 and 4 describing the procedure with continuous recovery of guanidine nitrate.

EXAMPLE 1

The reaction in the production of guanidine nitrate must be carried out in a homogenous melt of urea and ammonium nitrate containing granules of silicagel having a micron number of 20–100 in the form of a suspension.

The ratio urea:ammonium nitrate shall be a weight ratio of 1:2 during the entire 2½ to 4 hours of reaction. The quantitative addition of urea during the reaction is carried out depending on the consumption of ammonium nitrate.

In the below example the urea present in the beginning of the process is 60 kgs and the ammonium nitrate used amounts to 120 kgs. Thus an excess of ammonium nitrate is present. The ratio urea:ammonium nitrate is 1:2. In a first conversion step 15 kgs of urea and 10 kgs of ammonium nitrate are used because the conversion is carried out at a ratio of 3:2 of urea:ammonium nitrate. Subsequently urea is added to the mixture in quantities corresponding to the quantity of urea, i.e. 10 kgs of urea in this case. Therefore after the first step of the process 55 kgs of urea and 110 kgs of ammonium nitrate are present in the melt, and the ratio of urea:ammonium nitrate is again fixed at 1:2.

The below table shows the initial course of the process in respect to consumption of urea and ammonium nitrate and addition of urea:

|  | Proportion of urea | Proportion of ammonium nitrate | ratio urea: ammonium nitrate |
|---|---|---|---|
| Beginning | 60 kgs urea | 120 kgs AN | 1:2 |
| Consumption | 15 kgs urea | 10 kgs AN |  |
|  | 45 kgs urea |  |  |
| Addition | 10 kgs urea |  |  |
|  | 55 kgs urea | 110 kgs AN | 1:2 |
| Consumption | 15 kgs urea | 10 kgs AN |  |
| Addition | 10 kgs urea |  |  |
|  | 50 kgs urea | 100 kgs AN | 1:2 |
| Consumption | 15 kgs urea | 10 kgs AN |  |
| Addition | 10 kgs urea |  |  |
|  | 45 kgs urea | 90 kgs AN | 1:2 |
| Consumption | 15 kgs urea | 10 kgs AN |  |
| Addition | 10 kgs urea |  |  |
|  | 40 kgs urea | 80 kgs AN | 1:2 |

If reaction is carried out in the same way with a theoretical consumption of urea:ammonium nitrate=1.5:1.0 moles, the ratio of urea:ammonium nitrate remains 1:2. Thus it is no longer necessary to work with a higher excess of ammonium nitrate. Thereby the yields of guanidine nitrate are increased and the formation of triazines is prevented. After 90–93% of urea has been consumed meaning the end of the reaction, the ratio of urea:ammonium nitrate is 1:5 to 1:6 (final phase).

EXAMPLE 2

Below another discontinuous process for the production of guanidine nitrate from urea and ammonium nitrate.

A melt consisting of
60.0 kgs of urea
120.0 kgs of ammonium nitrate temperature 120° C.
40.0 kgs of silicagel
is passed into the stirred reactors.
The mixture is heated.

At 186° C. a heavy reaction takes place to produce guanidine nitrate and ammonium carbamate. The addition of further urea is carried out within 1 to 1½ hours in a method as described in example 1.

Based on the above indicated used proportions of the various reactants the catalyst is added to ammonium nitrate plus urea in a ratio of 1:6 to 1:7. Hereby it is possible to complete the conversion at 182°–192° C. within about 3 to 4 hours.

In the well-known processes for the recovery of guanidine nitrate big quantities of silicagel as a catalyst are used in a ratio to urea:ammonium nitrate to obtain no triazines but high conversion rates. British Pat. No. 923,272, at page 3, line 125, mentions that the initial molecular proportions of urea:ammonium nitrate:silicagel are 2:2:1.7 and as per page 3, line 55, a conversion rate of 75% is achieved whereas according to the present invention a ratio of urea:ammonium nitrate:catalyst of 3:3:1.0 is used and the conversion of urea into guanidine is 88–90%.

The formation of guanidine nitrate is determined by measuring the resulting ammonium carbamate and the urea is added so that the ratio urea:ammonium nitrate remains 1:2 minimum.

In the final phase the ratio of urea:ammonium nitrate is increased in favour of the ammonium nitrate up to 1:5 to 1:6.

With the beginning of the reaction up to its completion 1/6 of the ammonia recovered from the ammonium carbamate is passed through the reaction mass. This increases the pH value from 9.0–9.3 up to 9.8–10.2.

On completion of the melt the reaction mass consists of:

| | |
|---|---|
| 110.0 kgs | of guanidine nitrate |
| 49.0 kgs | of ammonium nitrate |
| 8.0 kgs | of urea |
| 1.0 kg | of by products |
| 40.0 kgs | of silicagel |
| 72.0 kgs | of ammonium carbamate consisting of |
| | 31.4 kgs $NH_3$ and 40.6 kgs of $CO_2$ |
| 280.0 kgs | |

Out of the 72 kgs of ammonium carbamate 12 kgs are disintegrated in a well-known manner. The resulting 5.23 kgs of ammonia are used to increase the alkalinity to 9.8–10.2 of the subsequent reaction mass.

120.0 kgs of wash-water from preceding batches are incorporated in the melt. 328.0 kgs will result containing 40 kgs of silicagel as a suspension in addition to the soluble reactants.

The filtration is carried out at above 90° C. The catalyst is treated with wash-water from preceding batches several times until no guanidine nitrate can be found any longer.

To the hot filtrate containing about 1 kilo of triazines a binder is added for the precipitation of the triazines at an adjusted pH value not above 4.0. The triazines are precipitated from the solution in a quantity of up to 80% and are separated off by another filtration. The existing filtrate is cooled to 0° C. and the crystallized-out guanidine nitrate is removed, washed again with wash solution at 0° C. and dried.

108.0 kgs of guanidine nitrate with a purity of 98.5–99.2% is obtained. 108.0 kgs of guanidine nitrate correspond to a yield of 88.5% related to the employed and consumed urea and 98.0% related to ammonium nitrate.

2.0 kgs of guanidine nitrate and 8.0 kgs of urea remain in the wash-waters and may be further processed into guanidine nitrate when working up the first wash-water containing 65% of the 2 kgs of guanidine nitrate and 65% of the 8 kgs of urea into anhydrous ammonium nitrate under reduced pressure and refluxing together with the ammonium nitrate anhydrously recovered by neutralization of the ammonium carbamate by means of nitric acid.

When carrying out ten tests in a series using the above wash-water, the yield of 98.5–99.2% guanidine nitrate amounts to 93.5–94.0% in the average. It must be taken into consideration that in each further batch no longer 120 kgs of ammonium nitrate but only 71–75 kgs are to be added. Furthermore continuously a regenerated catalyst free of deposited triazine is introduced into the cycle.

EXAMPLE 3

Continuous recovery of guanidine nitrate from urea and ammonium nitrate and nitric acid in the presence of silicagel resp.: The reaction is carried out continuously in four stirred reactors in a series.

Into reactor 1 a mixture consisting of 27.2% of urea, 54.5% of ammonium nitrate and 18.3% of catalyst, i.e. in a ratio of urea:ammonium nitrate = 1:2 is introduced at a reaction temperature of 150° C. under stirring in quantities identical to those discharged into the other reactors.

This mixture corresponds to the initial compound described in Example 2, discontinuous operation. The temperature in stirred reactor 2 is 186° C. The average residence time in reactor 2 is 40 minutes. The conversion of urea with ammonium nitrate is 40–45%, i.e. the ratio urea:ammonium nitrate would be 1:4 but during the reaction additional urea is added in such a way that the ratio urea:ammonium nitrate is maintained at about 1:2. The same conversion takes place in stirred reactor 3, also at 186° C. and a residence time of 80 minutes.

The melt leaving reactor 3 consists of
9.5% of urea
29.5% of ammonium nitrate
44.0% of guanidine nitrate
17.0% of catalyst
and from this a conversion of urea/ammonium nitrate of 65% results the ratio of urea:ammonium nitrate being 1:3.

In the fourth reactor an after-reaction is carried out at 186° C. during 70 minutes without further addition of reactants.

The melt running off continuously consists of

| | | |
|---|---|---|
| 10 kgs of urea | 5.0% | |
| 38 kgs of ammonium nitrate | 18.5% | ratio urea |
| 115 kgs of guanidine nitrate | 56.0% | to ammonium |
| 2 kgs of ammelide and melamin | 1.0% | nitrate being 1.4% |
| 40 kgs of catalyst | 19.5% | |
| 205 kgs | | |

75 kgs of ammonium carbamate are formed during the reaction step and are leaving the reactors in a gaseous condition and are converted into ammonium nitrate and $CO_3$ by means of 50% nitric acid. With the 38 kgs of ammonium nitrate + 10 kgs of urea and 3 kgs of guanidine nitrate in the shape of a 50% aqueous solution 82 kgs of ammonium nitrate as a 60% aqueous solution coming from the neutralization of ammonium carbamate with $HNO_3$ are evaporated together at 10–15 Torr and 130° C. down to less than 0.2% water and incorporated in the next batches to produce guanidine nitrate.

In this manner guanidine nitrate with more than 94% yield related to urea and 97% related to used nitric acid is produced by means of urea and nitric acid in the presence of silicagel.

EXAMPLE 4

Continuous production of guanidine nitrate from urea and nitric acid in the presence of silicagel.

In three stirred reactors of 400 liters capacity each and installed in the form of a cascade connected with each other at the lower end by a tube, the continuous conversion of urea with ammonium nitrate is carried out. Below please find a description of the parts (in weight) of the initial chemicals in the three reactor steps and the used chemicals, yields of guanidine nitrate, by-products and catalyst consumption during a production period of 111 hours.

Into stirred reactor 1, 150° C. hot melt consisting of
60 kgs of urea
120 kgs of ammonium nitrate
40 kgs of silicagel catalyst
is introduced.

The reaction temperature amounts to 185°–188° C. With passing of ammonia through the melt, after 40 minutes 20% of the urea is converted into guanidine nitrate.

The melt from stirred reactor 1 is passed into stirred reactor 2 and consists of
48 kgs of urea
113 kgs of ammonium nitrate
11 kgs of guanidine nitrate
40 kgs of catalyst
and the stirred reactor 1 is again filled with the same melt as mentioned above.

During 70 minutes another 60 kgs of urea is added successively under continuous passage of ammonia. 70% of the urea has been converted into guanidine nitrate, the resulting melt consists of
33 kgs of urea
65 kgs of ammonium nitrate
82 kgs of guanidine nitrate
40 kgs of catalyst.
53 kgs of gaseous ammonium carbamate are discharged.

This melt is passed into stirred reactor 3 in which the melt is subjected to an after-reaction at 188° C. with introduction of ammonia. The conversion of urea amounts to 94% related to employed urea. The melt continuously leaving reactor 3 consists of 6 kgs of urea
42 kgs of ammonium nitrate
115 kgs of guanidine nitrate
2 kgs of triazines
40 kgs of catalyst.

In total, 75 kgs of ammonium carbamate have been formed which are transferred in a gaseous condition to further processing steps.

The melt is quenched with wash-waters from preceding batches in quantities as leaving stirred reactor 3 and is worked up into guanidine nitrate as described in the preceding example.

The reaction is carried out continuously in the three reactors by the communicating pipe joint connection of the three reactors and not discontinuously. On completion of the continuous working period lasting 111 hours 12,765 kgs of guanidine nitrate 98.5/99% are obtained. The yield is 94% related to the employed urea.

Furthermore
4,300 kgs of 99% ammonium carbamate
2,400 kgs of pure carbon dioxide
are obtained.

For this process
13,320 kgs of urea
8,890 kgs of ammonium nitrate and
112 kgs of catalyst
have been used.

Hereby the 8,890 kgs of ammonium nitrate have been recovered from 7,000 kgs of nitric acid and 1,890 kgs of ammonia the latter being recovered from part of the ammonium carbamate.

Ammonium carbamate may be supplied to the fertilizer industries as such or processed into ammonium salt, e.g. ammonium nitrate, by means of a mineral acid.

As already described above, according to a well-known continuous production method for guanidine nitrate, the heated mixture of urea and ammonium nitrate is passed through a tubular, vertical reactor with a diameter of approx. 2.5 cms. To obtain suitable yields of guanidine nitrate in the performance of the well-known process, the reactor column has to be filled with silicic acid catalyst up to a mark of approx. 61 cms.

As detailed in the present invention, the well-known process is not suitable for application in industrial scale. Additionally it is to be pointed out that the gas formed during the reaction depends on the thickness of the reaction mass and increases its volume with rising height per cross-section of the reactor column. When the reaction mass is heavily admixed with gas, however, the heat transfer is becoming worse and worse in the reaction mass so that the heating temperature of the reaction mixture must be increased to obtain sufficient difference in temperature between reaction temperature and heating temperature of the mixture even in the upper part of the reactor column.

However, as an increase of the heating temperature results in considerable foaming and moreover in the formation of triazines, it is desirable to exceed the difference in temperature between heating temperature and reaction temperature during the reaction by not more than 5°–20° C.

It appears that also with such small differences between heating and reaction temperatures foaming during the reaction period can be avoided. The disadvantage of foaming is, a.o., that when removing foam also catalyst is discharged. On one hand this is uneconomic and on the other hand the proportion of catalyst compared to the reaction mass is changed uncontrollably.

Preferably the process of the invention is carried out at a heating temperature of around 5°–20° C. above the reaction temperature of the reactants not exceeding 190° C. to max. 210° C. and being maintained at this figure during approx. 100–240 minutes. However, the reaction in question being endotherm, it must be avoided that within the reaction mass there is a temperature drop. This is achieved because the reaction mass exists as a layer formed by a melt of urea, ammonium nitrate and catalyst which layer has a thickness between 1 and 30 cms, preferably 2 to 10 cms.

For a continuous performance of the reaction, it is preferred to continuously move the reaction mass as a melt into a flow of the above thickness, to add the required proportions of urea and possibly catalyst along the flow of the melt and, after conversion the continuously drained reaction mixture is mixed with wash-water, separated from the catalyst, cooled to 0° C. to −3° C. and the guanidine nitrate is recovered by centrifugation and dried.

According to another object of this invention, a reactor system for the performance of the process of the invention consists of one or several substantially horizontally arranged, tubular, heatable reactors in a series having an inlet into which the reaction mass is passed continuously together with the catalyst as a melt and is moved by means of a stirrer and conveying device and drained at an outlet of the reactor system whereby at one or several places before the outlet of the reactor system inlet nozzles are provided in certain distances to supply urea and catalyst.

Alternatively the reaction mass may also be passed on one or several heatable conveyor belts in series onto which the reaction mass is brought in a layer of desired thickness and is to be combined with the desired additives along the conveyor whereby the speed of the conveyor belt depending on the reaction rate of the reaction mixture can be chosen with the purpose of a continuous operation.

From the above mentioned, any expert in this field will be able to see that naturally numerous devices well-known in chemical technology, e.g. for drying of substances, with only little constructive expenditure may be modified for the performance of the process of the invention as far as such devices are able to convey a reaction mixture of a certain thickness at a determinable speed. Therefore there is no need to list such possible device known to each chemist. On the grounds of the attached drawings two examples are to describe devices for the performance of the process of the invention whereby FIG. 1 shows a reactor system for the continuous production of guanidine nitrate as a perspective, and FIG. 2 shows a conveyor for a continuous operation.

Figure 2:
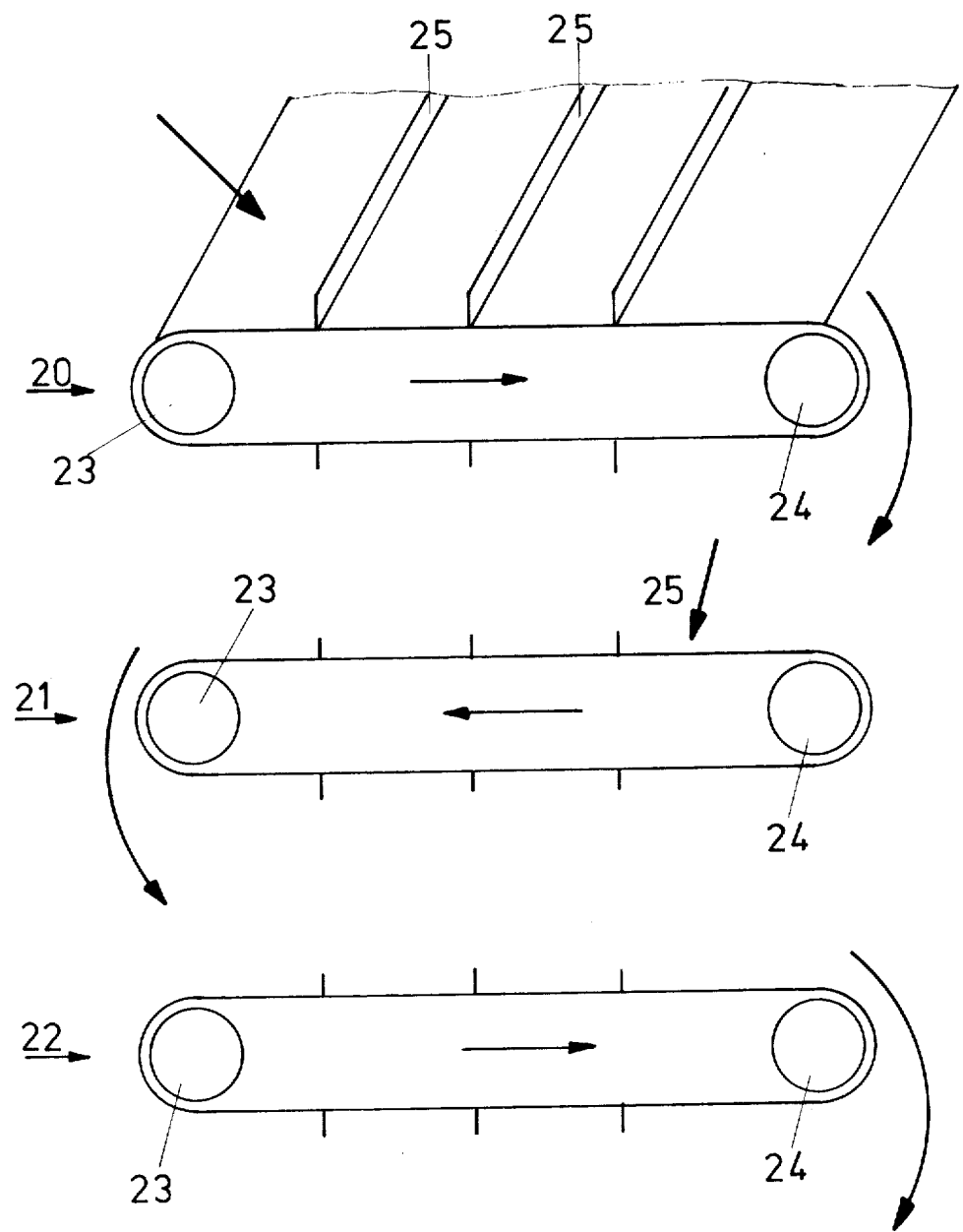

According to FIG. 1 the reactor system for a continuous production of guanidine nitrate consists of three substantially identical reactors 1, 2, 3 in a series. Basically also only one or two or even more reactors might be used when chosing a suitable length.

Each reactor 1, 2 or 3 includes an inner tube (4) in the form of an elongated vat with a cross section similar to an "U". The inner tube (4) is covered by a double-jacket (5) at least on a part of its wall. Approximately in the longitudinal axle centre of vat (4) a rotating shaft (7) has been installed provided with mixing plates (6). To give a better view, in the drawing only one mixing plate (6) has been shown but such mixing plates are installed along shaft (7) in certain distances from one to the other. Some of these mixing plates (6) have rotor areas in the form of propellers to effect a move of the reaction melt consisting of a mixture of ammonium nitrate, urea and catalyst introduced on the one face of vat (4) towards the other face opposite. If required, the direction of rotary motion of shaft (7) may be changed to adjust the reaction time within one reactor as desired.

In the space formed between the two tube-walls (4) and (5) steam of about 15–20 atü at around 200° C. is introduced into vat (4) to raise the temperature of the reaction mass. Due to the relatively big area of the wall of reactor vat (4) related to its depth practically not exceeding approx. 20 cms it has been ascertained that an even distribution of temperature in the reaction mass is possible not exceeding 5°–20° C. above reaction temperature of the reactants when operating shaft (7). Reactor vat (4) moreover is surrounded by a lower part (8) and a cap (9) that can be freely moved upwards and downwards forming the exterior jacket of the vessel which may also be heated with steam (15). Along the upper edge of the lower part (8) a circular drain has been provided serving to take up the lower edge of cap (9). The drain (10) has been filled with a mixture of urea and ammonium nitrate for sealing reasons, or with another liquid seal suitable for the temperature in question. If during the reaction the inner pressure in reactor vat (4) is increased the cap (9) is lifted by a pressure control, e.g. counter-weight which can be adjusted (not shown in the drawing). Hereby the reaction mixture is not subjected to increased pressure which is, for safety reasons, necessary for chemical compounds containing ammonium nitrate.

The liquid seal in drain (10) thereby provides uninterrupted sealing effect. In the bottom of the vat (4) a tube (12) for the supply of ammonia used to control the pH value of the mixture is provided.

The throughput rate of the reaction mixture through reactor 1 may be determined by controlling the rotation rate of shaft (7) and by changing the direction of its rotary motion resp.

In the described example the reaction mass enters reactor (2) coming from reactor (1) after a certain reaction period. To maintain the weight ratio of the reactants urea and ammonium nitrate, an inlet (11) for urea has been provided in reactor (2). Moreover reactors (1) and (2) are completely identical in their construction.

The reaction mixture reacts in reactor (3) and finally leaves this reactor at the outlet to be washed with washwater and separated from the catalyst. The guanidine nitrate is recovered by centrifugation and subsequent drying.

FIG. 2 shows a conveyor consisting of three circular conveyor belts (20, 21, 22) made of heatable metal. The conveying rate and the direction of move of each conveyor belt is determined by guide rollers (23) and (24). The reaction mixture consisting of urea, ammonium nitrate and catalyst is brought on conveyor belt (20). Separating walls (25) provided transversely towards the direction of the conveyor belts (20, 21, 22) have to dose the reaction mass and limit their maximum thickness.

After passage over the first conveying track (20) the reaction mass is passing to conveyor belt (21). To maintain the ratio of the mixture urea:ammonium nitrate, an urea inlet (25) has been provided at the beginning of conveyor belt (21). The after-reaction is carried out on conveyor belt 22 at the end of which the reaction product is processed according to the already described quenching process.

Due to the present low thickness of the layers of the reaction mixture in relation to the large heated surface of the conveyor belts it is sufficient to adjust the heating temperature at only few degrees above the reaction temperature. This is of considerable advantage because only quite insignificant quantities of by-products will be formed during reaction. So, for example, a heating temperature of 190° C. will be high enough for a reaction temperature of 187° C. to effect reaction. Thereby no triazines can be formed. Moreover no foaming has to be feared due to so small differences in temperature.

What is claimed is:

1. In a process for the manufacture of guanidine nitrate wherein urea is reacted with ammonium nitrate in the presence of silica gel, the improvement comprising carrying out a reaction of said urea and ammonium nitrate wherein the initial mixture of urea and ammonium nitrate contains about a 1:2 weight ratio of urea to ammonium nitrate, heating the initial mixture to an elevated temperature of about 5°–20° C. above the reaction temperature of the urea and ammonium nitrate reactants not exceeding a maximum temperature of about 210° C., separating the formed guanidine nitrate from the reaction mixture, and gradually adding urea to the reaction mixture in such quantities relative to the reaction mixture such that the weight ratio of urea to ammonium nitrate is always about 1:2 up to the final phase of the reaction wherein 90–93% of urea has been consumed, after which the ratio of reactants increases in favor of ammonium nitrate.

2. The process of claim 1 wherein at the beginning of the process the weight ratio of urea:ammonium nitrate is 1:2 and during the course of the process urea is added stepwise in an amount corresponding to about ⅔ of the urea consumed in the process for the formation of guanidine nitrate and during the process up to the final phase of the reaction the ratio of urea:ammonium nitrate is maintained at about 1:2 and increased in favor of the ammonium nitrate to about 1:5 to 1:6 in the final phase of the reaction.

3. The process of claims 1 or 2 wherein the catalyst is added to the reaction mixture stepwise so that its efficiency is always substantially the same during the process.

4. The process of claims 1 or 2 wherein the catalyst is added to the reaction mixture in increasing quantities during the process.

5. The process of claims 1 or 2 wherein the catalyst is regenerated after several series of throughput and is reused for the succeeding batches.

6. The process of claims 1 or 2 wherein the catalyst is used in quantities of 10–20% related to the initial mixture of urea and ammonium nitrate.

7. The process of claim 2 wherein ammonium carbamate is formed during the reaction of urea with ammonium nitrate and a portion of the ammonium carbamate is disintegrated into ammonia and $CO_2$ and the obtained ammonia is passed through the reaction mixture so that the pH value of the mixture is increased from 9.0 to 9.3 up to about 9.8 to 10.2.

8. The process of claim 7 wherein the ammonia formed during conversion is converted into ammonium nitrate by means of nitric acid and the latter is reused.

9. The process of claim 2 wherein the guanidine nitrate formed during the process is separated from the catalyst as a hot solution and mixed with binders to bind the organic substances present in the solution and to filter them off.

10. The process of claim 9 wherein the separation of the final product is made without recrystallization from the aqueous solution after cooling.

11. The process of claim 10 wherein the filtrate contains about 40–60% of ammonium nitrate, 1–3% urea, 1–2% guanidine nitrate, 0.1–0.3% ammelide and is suitable for further use as a fertilizer.

12. The process of claim 2 wherein the reaction is maintained at the elevated temperature for approximately 100 to 240 minutes.

13. The process of claim 12 wherein the reaction mass is present as a melt formed by urea, ammonium nitrate and catalyst, the thickness of which is 1 to 30 cms.

14. The process of claim 13 wherein the thickness is 2 to 10 cms.

15. The process of claim 13 wherein the reaction mass is moved in a flow and the required urea and catalyst are added as needed along the flow of the melt and after completing conversion the reaction mixture is mixed with wash-water, separated from the catalyst, cooled to 0° to −3° C. and the guanidine nitrate is recovered by centrifugation and dried in a quenching stage.

16. The process of claim 15 wherein the reaction mass is continuously passed through at least one substantially horizontal heatable autoclave and after completion of the reaction of the reactants the mass is introduced into the quenching stage.

17. The process of claim 16 wherein there are several substantially horizontal heatable autoclaves in a series.

* * * * *